United States Patent [19]
Ohno et al.

[11] Patent Number: 6,054,596
[45] Date of Patent: Apr. 25, 2000

[54] PROCESS FOR PRODUCING CYCLIC CARBONIC ESTERS

[75] Inventors: Mitsuru Ohno, Tsukuba; Shuichi Yamagiwa, Matsudo, both of Japan

[73] Assignee: Daicel Chemical Industries, Ltd., Osaka, Japan

[21] Appl. No.: 09/271,213

[22] Filed: Mar. 17, 1999

[30] Foreign Application Priority Data

Mar. 19, 1998 [JP] Japan .................................. 10-070073

[51] Int. Cl.$^7$ ...................... C07D 317/36; C07D 317/38; C07D 319/06; C07D 321/06
[52] U.S. Cl. ........................... 549/228; 549/229; 549/230
[58] Field of Search ................... 549/228, 229, 549/230

[56] References Cited

U.S. PATENT DOCUMENTS

| | | | |
|---|---|---|---|
| 2,441,298 | 5/1948 | Strain | 260/77.5 |
| 3,426,042 | 2/1969 | Hostettler et al. | 260/340.2 |
| 3,663,569 | 5/1972 | Lew | 260/340.2 |
| 5,091,543 | 2/1992 | Grey | 549/228 |
| 5,212,321 | 5/1993 | Muller et al. | 549/228 |

FOREIGN PATENT DOCUMENTS

| | | |
|---|---|---|
| 04 22 523 | 4/1991 | European Pat. Off. . |
| 34 18 091 | 11/1985 | Germany . |
| 256356B2 | 11/1990 | Japan . |
| 09235252A | 9/1997 | Japan . |

OTHER PUBLICATIONS

*Encyclopedia of Reagents for Organic Synthesis*, vol. 6, p.4107–4109, 1995.

*Journal of American Chemical Society*, vol. 68, p.729, 780–789 (Jan.–Jul. 1946).

Bin, Hu. *Chemical Abstracts*, Columbus Ohio, US, vol. 130, No. 19, p. 780, (1999).

Takano et al, Heterocycles, vol. 29 (9), pp. 1849–1853, 1989.

*Primary Examiner*—Ba K. Trinh
*Attorney, Agent, or Firm*—Birch, Stewart, Kolasch & Birch, LLP

[57] ABSTRACT

Reacting a diol (1) with a carbonic ester (2) to produce a cyclic carbonic ester (3) using a salt of a weak acid with an alkaline metal or alkaline earth metal as a catalyst. The diol (1) contains diols having an asymmetric carbon atom. The reaction mixture is neutralized and distilled to obtain a cyclic carbonic ester. Cyclic carbonic esters are produced using an easily accessible and easy to handle reactant, with good yield and under mild and moderate conditions.

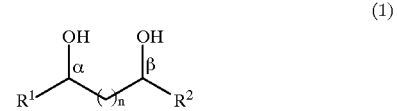

(1)

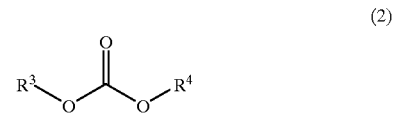

(2)

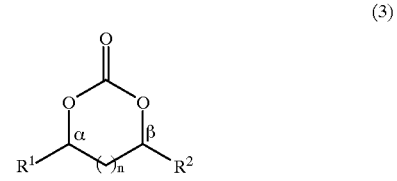

(3)

13 Claims, No Drawings

PROCESS FOR PRODUCING CYCLIC CARBONIC ESTERS

FIELD OF THE INVENTION

The present invention relates to a process for producing cyclic carbonic esters having a variety of potential applications such as intermediates of medicinal substances and raw materials of polyesters and other materials.

BACKGROUND OF THE INVENTION

A cyclic carbonic ester is generally synthesized by condensing a diol or its reactive equivalent or synthon with carbonic acid or its derivative. For example, Japanese Patent Application Laid-open No. 235252/1997 (JP-A-9-235252) discloses a method for synthesizing a cyclic carbonic ester from oxyrane and carbon dioxide by ring expansion, and there is disclosed in the Encyclopedia of Reagents for Orgnaic Synthesis, vol. 6, p.4108 a method of synthesizing cyclic carbonic esters using a diol and phosgene. These methods, however, require the use of specific material, i.e., oxirane or phosgene, which is hard to obtain. Besides, oxirane is highly explosible and phosgene is of high toxicity and therefore dangerous and require handling with care. For such reasons, commercial operation according to the above methods has difficulties.

Synthesis of a cyclic ester from a diol and a carbonic ester has been known as one way to solve the problem of handling. For example, U.S. Pat. No. 2,441,298 discloses a process for synthesizing ethylene carbonate from ethylene glycol and diethyl carbonate using sodium metal as a catalyst. U.S. Pat. No. 3,663,569 discloses a process of synthesis using a dialkyl or aryl tin oxide as a catalyst, and U.S. Pat. No. 5,091,543 discloses a process of synthesis using an alkyl ammonium salt, tertiary amine, or an ion-exchange resin containing those as a catalyst. However, sodium metal as a catalyst has possibility of explosive reaction on contact with water, and handling with care is also needed. On the other hand, the dialkyl or aryl tin oxide, and alkyl ammonium salts, and the like are not the catalysts of general-purpose and are hard to obtain.

For a better handling-convenience or accessibility, Japanese Patent Application Laid-open No. 56356/1990 (JP-B-2-56356) proposes and discloses a process for producing cyclic carbonic esters by, with the aid of potassium carbonate as a catalyst, stirring trimethylolpropane and diethyl carbonate in a packed column and gradually vacuuming up the column while evaporating ethanol being by-produced. This literature says that 6-membered-ring cyclic esters are also obtainable (yield: 91%) by dissolving the reaction mixture in a mixed solvent of methylene chloride/dioxane (1:1), making the resultant mixture flow over a crosslinked polystylene beads polymer, evaporating the solvent under reduced pressure for preliminary purification, gradually feeding the preliminary-purified product dropwise into a flask having been heated to 220° C. in advance under reduced pressure for distillation, and trapping the distillate with liquid nitrogen. This method, however, is disadvantageous in commercial terms because the reaction is effected in the packed column. Moreover, this method involves many steps such as reaction, solvent-evaporation, dissolution, absorption, solvent-evaporation and distillation and therefore troublesome and complicated.

U.S. Pat. No. 3,426,042 discloses a process of synthesis of cyclic carbonic esters from glycol and diethyl carbonate using sodium hydroxide as a catalyst. But this literature fails to refer to its yield, not describing in further detail. Further, Journal of American Chemical Society, vol. 68 (1946), p.783 discloses a process in which ethylene carbonate is formed from ethylene glycol and diethyl carbonate using potassium carbonate as a catalyst and from which a cyclic carbonic ester is isolated by crystallization. In this method, however, the yield of the object compound is low (51 to 55%) and such low yield is not sufficient for practical commercial operation. Furthermore, although the isolation by crystallization is effective for ethylene carbonate (melting point: 37 to 39° C.), not all object compounds are covered by this method. In the case where the object product is a cyclic carbonic ester having a low melting point, for example, a 6-membered-ring cyclic carbonic ester (propylene carbonate), the isolation by crystallization is not effective due to the melting point as low as −55° C., and rather difficult. A product having a low melting point can be isolated by distillation, for example, by flash evaporation or thin film evaporation. The distillation of the reaction product according to the above-mentioned method, however, leads to the hydrolysis or reverse reaction of the reaction product and thus results in the decomposition of the object compound. Particularly, the use of an optically active substance as a reactant leads to the loss of its optical activity and racemization thereof.

SUMMARY OF THE INVENTION

Accordingly, an object of the present invention is to provide a process for producing cyclic carbonic esters with good yield and in a simple manner, using an easily accessible and easy-to-handle reactant.

Another object of the present invention is to provide a process for producing cyclic carbonic esters with good yield and in a simple manner, even if the object compound has a low melting point.

Further another object of the present invention is to provide a process for producing optically active cyclic carbonic esters.

The inventors of the present invention made extensive studies to achieve the above objects and found that a cyclic carbonic ester can be produced with good yield and in a simple manner by reacting a certain diol with a carbonic ester using a salt of a weak acid with an alkali metal or alkaline earth metal as a catalyst, and that even when an optically active substance is used as a reactant, its optical activity is retained. The present invention has been accomplished based on the above findings.

Thus, in the process of the present invention for producing cyclic carbonic esters (cyclic carbonic acid esters), in the presence of a salt of a weak acid with an alkali metal or alkaline earth metal, a diol shown by the following formula (1):

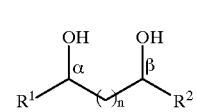

(1)

wherein n denotes an integer of 0 to 5, $R^1$ and $R^2$ are the same or different and each represents a hydrogen atoms or a non-reactive organic group, and may bond together to foam a ring together with the adjacent carbon atoms, with the proviso that $R^1$ and $R^2$ are not concurrently hydrogen atoms in the case of n=0 is reacted with a carbonic ester (carbonic acid ester) shown by the following formula (2):

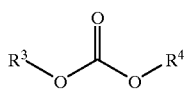
(2)

wherein $R^3$ and $R^4$ are the same or different and each represents a non-reactive organic group, and may bond together to form a ring together with the adjacent oxygen atoms to produce a cyclic carbonic ester shown by the formula (3):

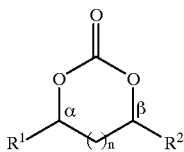
(3)

wherein $R^1$, $R^2$ and n have the same meanings as defined above.

The non-reactive organic groups represented by $R^1$ and $R^2$ may be alkyl groups, and the non-reactive organic groups represented by $R^3$ and $R^4$ may be alkyl groups or aryl groups. The weak acid salt includes carbonates, hydrogencarbonates, carboxylates, oxycarboxylates, etc. Moreover, in the reaction, a cyclic carbonic ester shown by the formula (3) may be formed while maintaining or retaining the steric configuration of an asymmetric carbon atom of a diol shown by the formula (1) in which at least one of the carbon atoms at the α-position and the β-position.

In the process of the present invention, the reaction product produced by the reaction of a diol of the formula (1) with a carbonic ester of the formula (2) may be neutralized. After the neutralization, the reaction mixture may further be subjected to distillation.

DETAILED DESCRIPTION OF THE INVENTION

[Diol]

The diol used in the present invention is shown by the formula (1) (hereinafter, referred to simply as diol (1)). In the formula (1), n is, e.g., 0 to 5, preferably 0 to 3, and more preferably 1 to 3. Examples of the non-reactive organic groups represented by $R^1$ and $R^2$ are alkyl groups, alkenyl groups, alkynyl groups, aryl groups, heterocyclic groups, etc.

As the alkyl groups, there may be exemplified straight- or branched-chain $C_{1-20}$) (preferably, $C_{1-8}$, more preferably $C_{1-6}$, and particularly $C_{1-4}$) alkyl groups such as methyl, ethyl, propyl, isopropyl, butyl, s-butyl, t-butyl, pentyl, isopentyl, isohexyl, heptyl, and octyl groups; and $C_{3-10}$ (preferably, $C_{3-6}$) cycloalkyl groups such as cyclopropyl, cyclobutyl, cyclopentyl, cyclohexyl, and cyclooctyl groups.

As the alkenyl groups, there may be exemplified straight- or branched-chain $C_{2-18}$ (preferably, $C_{2-10}$, particularly $C_{2-5}$) alkenyl groups such as vinyl, allyl, isopropenyl, 1-butenyl, 2-butenyl, and 2-hexenyl groups; and $C_{3-10}$ (preferably $C_{3-6}$) cycloalkenyl groups such as cyclopropenyl, cyclobutenyl, cyclopentenyl, cyclohexenyl, and cyclooctenyl groups.

As the alkynyl groups, there may be exemplified straight- or branched-chain $C_{2-18}$ (preferably $C_{2-10}$, particularly $C_{2-5}$) alkynyl groups such as ethynyl, propynyl, 1-butynyl, 2-butynyl, 1-heptynyl groups; and $C_{3-10}$ cycloalkynyl groups such as cyclopropynyl, cyclobutynyl, cyclopentynyl, cyclohexynyl, and cyclooctynyl groups.

The aryl groups include $C_{6-14}$ (preferably, $C_{6-10}$) aryl groups such as phenyl and naphthyl groups.

The heterocycles corresponding to the above-mentioned heterocyclic groups include heterocycles containing an oxygen atom as a heteroatom (e.g., 5-membered rings such as furan, oxazole, isooxazole, and tetrahydrofuran; 6-membered rings such as pyran; and condensed or fused rings such as benzofuran, isobenzofuran, dibenzofuran, xanthone, xanthene, chroman, isochroman, and chromene); heterocycles containing a sulfur atom as a heteroatom (e.g., thiophene, thiazole, isothiazole, thiadiazole, and benzothiophene); and heterocycles containing a nitrogen atom as a heteroatom (e.g., 5-membered rings such as pyrrole, pyrazole, imidazole, triazole, and pyrrolidine; 6-membered rings such as pyridine, pyridazine, pyrimidine, pyrazine, piperidine, and morpholine; and condensed or fused rings such as indole, indolene, isoindole, indazole, indoline, isoindoline, quinoline, isoquinoline, quinolinequinoline, quinoxaline, quinazoline, phthalazine, purine, carbazole, acridine, naphthoquinoline, phenanthrodine, phenanthroline, naphthyridine, benzoquinoline, phenoxazine, phthalocyanine, and anthracyanine).

These non-reactive organic groups may have a substituent, and any substituent is possible provided that it does not adversely affect the reaction. For example, there may be mentioned halogen atoms (e.g., chlorine atom, bromine atom), alkoxy groups (e.g., $C_{1-10}$ alkoxy groups such as methoxy and ethoxy groups), aryloxy groups (e.g., $C_{6-14}$ aryloxy groups such as phenyloxy group), substituted-amino groups (e.g., di-$C_{1-6}$ alkyl-substituted amino groups such as dimethylamino group), acyl groups (e.g., $C_{2-10}$ acyl groups such as acetyl and benzoyl groups), acyloxy groups (e.g., $C_{2-10}$ acyloxy groups such as acetoxy and benzoyloxy groups), and alkoxycarbonyl groups (e.g, $C_{2-10}$ alkoxycarbonyl groups such as methoxycarbonyl and ethoxycarbonyl groups).

As to the ring formed with $R^1$ and $R^2$ bound to each other and the adjacent carbon atoms, there may be exemplified $C_{3-15}$ cycloalkane rings such as cyclopropane, cyclobutane, cyclopentane, cyclohexane, cycloheptane, cyclooctane, and cyclododecane rings.

Preferred as $R^1$ and $R^2$ are, e.g., hydrogen atom, alkyl groups, alkenyl groups, alkynyl groups, cycloalkyl groups, and aryl groups. Hydrogen atom and alkyl groups (e.g., $C_{1-6}$ alkyl groups, particularly $C_{1-4}$ alkyl groups) are more preferable. As for the formula (1) shown above, the case where n is 0 and both $R^1$ and $R^2$ are hydrogen atoms is excluded.

Typical examples of the diol shown by the formula (1) are saturated $C_{3-10}$ alkylene glycols (particularly, saturated $C_{3-6}$ alkylene glycols) such as 1,2-propanediol, 1,2-butanediol, 1,3-butanediol, 1,3-pentanediol, 1,4- hexanediol, 4,6-nonanediol, and 1,2-octadecanediol; unsaturated $C_{4-10}$ alkylene glycols having a double bond or triple bond (particularly, unsaturated $C_{4-6}$ alkylene glycols), such as butenediols, pentenediols, hexenediols, nonenediols, octadecenediols, butynediols, pentynediols, hexynediols, nonynediols, and octadecynediols; cyclic $C_{4-10}$ alkylene glycols such as cyclohexanediols; and cyclic $C_{4-10}$ unsaturated alkylene glycols such as cyclohexenediols. These diols may have a substituent such as an alkyl group, aryl group, and a heterocyclic group. None of the above-mentioned saturated or unsaturated alkylene glycols has two hydroxyl groups at both ends. Examples of the preferred diols are asymmetric diols having an asymmetric carbon atom(s)(particularly, asymmetric saturated alkylene glycols, asymmetric unsaturated alkylene glycols, asymmetric cyclic alkylene glycols, asymmetric cyclic unsaturated alkylene glycols, etc.).

In the diol shown by the formula (1), at least one of the carbon atoms at the α-position and the β-position may be asymmetric. Even when such optically active diol is used, in the object compound cyclic carbonic ester of the formula (3), the steric configuration of the carbon at the α-position or the β-position is retained or maintained.

[Carbonic ester]

In the carbonic ester shown by the formula (2) (hereinafter, referred to simply as carbonic ester (2)), examples of the non-reactive organic groups represented by $R^3$ and $R^4$ are the same as those exemplified as to $R^1$ and $R^2$ in the formula (1).

Preferred as $R^3$ and $R^4$ are alkyl groups, cycloalkyl groups, aryl groups, and among others, alkyl groups (e.g., $C_{1-6}$ alkyl groups, particularly $C_{1-4}$ alkyl groups) and aryl groups (e.g., $C_{6-14}$ aryl groups, particularly $C_{6-10}$ aryl groups) are more preferable.

$R^3$ and $R^4$, if needed, may bond to each other to form a ring together with the adjacent oxygen atoms. As the ring to be formed, there may be exemplified 5 to 15-membered rings such as dioxolanes, dioxanes, dioxepanes, and dioxecanes. A noncyclic carbonic ester is usually employed as the carbonic ester.

Typical carbonic esters shown by the formula (2) are, e.g., symmetric or asymmetric di-$C_{1-6}$ alkyl carbonates such as dimethyl carbonate, ethyl methyl carbonate, diethyl carbonate, and di-t-butyl carbonate; symmetric or nonsymmetric aryl carbonates such as diphenyl carbonate and toluyl phenyl carbonate; alkene carbonates; and alkyne carbonates. An organic group in such carbonic ester may have a substituent such as an alkyl group, an aryl group, or a heterocyclic group. Preferred carbonic esters are those azeotropic with an alcohol formed by hydrolysis, such as di-$C_{1-2}$ alkyl carbonates (e.g., dimethyl carbonate).

[Catalyst]

As to the weak acid salt as a catalyst, the alkali metal includes, e.g., lithium, sodium, potassium, rubidium, and cesium, and the alkaline earth metal includes, e.g., magnesium, calcium, strontium, and barium. The alkali metal is preferably potassium or sodium, and the alkaline earth metal is preferably magnesium or calcium.

As the weak acid, there may be mentioned acids having a pKa of not less than 1 (not exceeding 15). For example, organic acids such as carboxylic acids (e.g., monocarboxylic acids such as formic acid, acetic acid, propionic acid, butyric acid, valeric acid, naphthenic acid, and stearic acid; polycarboxylic acids such as oxalic acid and maleic acid; and oxycarboxylic acids such as glycolic acid, lactic acid, malic acid, tartaric acid, and citric acid), and inorganic acids such as carbonic acid, phosphoric acid, and boric acid. Preferred as the weak acid salt are, e.g., salts of carboxylic acid [e.g., carboxylates (e.g., formates, acetates), polycarboxylates (e.g., oxalates)], oxycarboxylates (e.g., lactates), carbonates, hydrogencarbonates, phosphates (e.g., phosphates, hydrogenphosphates, dihydrogenphosphates), and borates (e.g., orthoborates, diborates, methaborates, pentaborates). Particularly, carboxylates, polycarboxylates, oxycarboxylates, carbonates, and hydrogencarbonates are preferable.

As the weak acid salt, there may be exemplified potassium formate, sodium formate, magnesium formate, calcium formate, potassium acetate, sodium acetate, magnesium acetate, calcium acetate, potassium lactate, sodium lactate, magnesium lactate, calcium lactate, potassium oxalate, sodium oxalate, magnesium oxalate, calcium oxalate, potassium carbonate, sodium carbonate, magnesium carbonate, calcium carbonate, potassium hydrogencarbonate, and sodium hydrogencarbonate.

These weak acid salt can be used singly or in a combination of two or more species.

[Production of cyclic carbonic esters]

The cyclic carbonic ester shown by the formula (3) (hereinafter, referred to simply as cyclic carbonic ester (3)) can be produced by reacting the diol (1) with the carbonic ester (2) in the presence of the catalyst. In the reaction, an alcohol corresponding to the carbonic ester (2) is liberated (hereinafter, referred to simply as by-product alcohol), which is expressed by, e.g., $R^3$—OH or $R^4$—OH ($R^3$ and $R^4$ have the same meanings as defined above).

The amount of the carbonic ester (2) relative to 1 mole of the diol (1) can suitably be selected in terms of reaction efficiency, economy, etc, and is 0.01 to 100 mole, preferably 0.1 to 10 mole, and more preferably 0.8 to 5 mole (e.g., 1 to 5 mole). When using an asymmetric diol as the diol (1), the carbonic ester (2) is used in an excess amount (not less than 1 mole), and the amount is generally 1 to 100 mole, preferably 1 to 10 mole and more preferably about 2 to 10 mole.

The amount of the catalyst relative to the diol (1) can suitably be selected, depending on the species of the diol (1), the carbonic ester (2), and the catalyst. The amount is, e.g., 0.001 to 1 mole, preferably 0.005 to 0.5 mole, and more preferably 0.01 to 0.2 mole.

In the reaction described above, when the equilibrium constant of the reaction is large, the reaction proceeds smoothly even with a smaller amount of the carbonic ester (2), producing the cyclic carbonic ester (3) with high yield. Moreover, the object compound can be obtained with high yield, even with a smaller amount of the carbnoic ester (2), by reacting those under distillation condition, in which the reaction is proceeded while removing one of the products (usually, by-product alcohol) from the system, e.g., by allowing the reaction to proceed while removing both by-product alcohol and carbonic ester (2) by azeotropy.

In the process of the present invention, the reaction of the diol (1) with the carbonic ester (2) is usually conducted in the absence of a solvent and may be carried in an organic solvent, if necessary. As the organic solvent, any solvent can be employed provided that it does not adversely affect the reaction. Examples of the organic solvent are aromatic hydrocarbons such as benzene, toluene, xylene, and ethylbenzene; aliphatic hydrocarbons such as pentane, hexane, heptane, and octane; alicyclic hydrocarbons such as cyclohexane and methylcyclohexane; halogenated hydrocarbons such as chloroform, dichloromethane, dichloroethane, chlorobenzene, chlorobutane, bromoform, and bromobenzene; alcohols such as methanol, ethanol, 2-propanol, and t-butanol; ketones such as acetone, methyl ethyl ketone, and isobutyl methyl ketone; ethers such as diethyl ether, diisopropyl ether, dibutyl ether, ethylene glycol dimethyl ether, dioxane, and tetrahydrofuran; esters such as ethyl acetate; nitriles such as acetonitrile; and aprotic polar solvents such as sulfur-containing compounds [e.g., sulfoxides (e.g., dimethyl sulfoxide), sulfones (e.g. sulfolane)], N, N-dimethylformamide, dimethyl sulfoxide. These solvents can be used singly or in a combination of two or more species.

In the case of the by-product alcohol being not azeotropic with the carbonic ester (2), the use of a solvent azeotropic with the by-product alcohol (e.g., ethyl acetate, hexane, toluene, chlorobutane) permits the azeotropy of the by-product with the solvent, removing the by-product out of the system. As a result, the reaction proceeds smoothly.

The reaction is usually effected at a temperature of about −30 to 200° C., preferably about −10 to 150° C., and more preferably about −10 to 100° C. (e.g., 20 to 100° C.). When using an optically active diol as the diol (1), the reaction temperature is usually about −30 to 120° C., preferably about −10 to 100° C., and more preferably about −10 to 70° C. (e.g., 0 to 70° C.) to prevent the racemization, and it may be room temperature or lower (e.g., about 0 to 40° C., particularly about 10 to 30° C.).

The reaction is usually effected at atmospheric pressure, and may be conducted under reduced pressure or under applied pressure, if necessary.

The reaction can be carried out in a conventional batch system, semi-batch system, or continuous system.

The cyclic carbonic ester (3) formed in such manner can be obtained after a conventional purification step, such as condensation, crystallization, column chromatography, and distillation. Preferably, the reaction mixture is neutralized. Particularly, it is preferable to obtain the object compound by neutralization followed by distillation. The neutralization can be conducted by mixing the reaction mixutre with an acid. A strong acid, practically an acid having a pKa of not more than 1, is usually employed as the acid. As the acid, e.g., use can be made of inorganic acids such as nitric acid, sulfuric acid, and hydrochloric acid; and organic acids such as sulfonic acids (e.g., methanesulfonic acid, trichloromethanesulfonic acid, p-toluenesulfonic acid). These acids can be used singly or in a combination of two or more species. The preferable acid includes inorganic acids (sulfuric acid or hydrochloric acid), and sulfuric acid is particularly preferred.

The amount of the acid for neutralization is usually about 0.5 to 3 equivalent (e.g., 0.7 to 1.5 equivalent) and preferably about 0.8 to 1.2 equivalent (e.g., 0.9 to 1.1 equivalent), relative to the amount of the catalyst (weak acid salt). The neutralization can be effected at a temperature at which the product is inhibited from decomposition and racemization (e.g., −20 to 100° C., preferably −5 to 50° C., and more preferably 0 to 30° C.).

The neutralization of the catalyst (weak acid salt) with an acid (e.g., a strong acid) makes the catalyst inactive, and the inactivated compound (e.g., strong acid salt or weak acid) can be removed by a conventional method such as filtration, centrifugation, and two-layer separation, if needed.

Whether the inactivated compound has been removed or not, a cyclic carbonic ester (3) of high purity can be obtained by subjecting the neutralized mixture to distillation for purification. The pressure and temperature at which the distillation is effected can be selected according to the boiling point of the cyclic carbonic ester (3). The pressure is usually about 0.1 to 200 mmHg and preferably about 0.1 to 100 mmHg (e.g., 0.5 to 10 mmHg), and the temperature is 20 to 200° C. and preferably about 50 to 150° C. (e.g., 70 to 120° C.). In the case where the object compound is an optically active cyclic carbonic ester, the pressure and temperature for distillation can be selected from the ranges of, e.g., usually 0.1 to 200 mmHg, preferably about 0.1 to 100 mmHg (e.g., 0.5 to 10 mmHg), and 20 to 150° C. and preferably about 20 to 100° C., respectively.

The cyclic carbonic esters formed according to the present invention can be utilized as intermediates of medicinal substances or raw materials of polyesters and other materials.

According to the process for producing cyclic carbonic esters of the present invention, cyclic carbonic esters can be produced under mild and moderate conditions with good yield, using a reactant easily accessible and easy to handle. Moreover, according to the present invention, even the production of cyclic carbonic esters having a low melting point is possible with good efficiency and in a simple manner. Further, the present invention also realizes the production of optically active cyclic carbonic esters.

EXAMPLE

The following examples are intended to describe the present invention concretely, but should by no means be construed to limit the scope of the invention.

Incidentally, unless stated otherwise, the products were characterized by gas chromatography by comparison with authentic samples.

Example 1 (Catalyst: $K_2CO_3$)

A 100 ml four-neck flask equipped with a reflux condenser and a thermometer was fed with 7.6 g (0.10 mol) of 1,2-propanediol (racemic body), 9.0 0g (0.10 mol, 1 equiv.) of dimethyl carbonate, and 0.69 g (0.005 mol, 0.05 equiv.) of potassium carbonate anhydride, and the mixture was stirred. The mixture in the flask was heated with an oil bath and refluxed at 90° C. for 3 hours.

After the completion of the reaction, the analysis of the mixture by gas chromatography revealed the formation of the object compound 4-methyl-1,3-dioxolan-2-one, and it was found that the conversion of 1,2-propanediol was 70% and the selectivity was 100%.

Having been heated and refluxed for another 2 hours, the object compound was formed with a 70% conversion of 1,2-propanediol and a 99% selectivity, and the reaction was completed Further, 3.6 g (0.040 mol, the total amount of dimethyl carbonate relative to 1,2-propanediol: 1.4 eguiv.) was added to the mixture, and the mixture was heated and refluxed. After 1 hour, there was formed 4-methyl-1,3-dioxolan-2-one with a 82% conversion of 1, 2-propanediol and a 95% selectivity. With the above results, the equilibrium constant of. this reaction system was calculated at 5.6.

Example 2 (Distillation of a cyclic carbonic ester)

A mixture of 15.2 g (0.20mol) of 1,2-propanediol (racemic body), 43.2 g (0.48 mol, 2.4 equiv.) of dimethyl carbonate, and 1.38 g (0.010 mol, 0.05 equiv.) of $K_2CO_3$ was heated and refluxed for 3 hours. In the reaction mixture, there was formed the object compound 4-methyl-1,3-dioxolan-2-one with a 89% conversion of 1,2-propanediol and approximately 100% selectivity.

The reaction mixture was cooled with an ice bath, and 0.99 g (I equiv. relative to $K_2CO_3$) of concentrated sulfuric acid (purity: 98 weight %) was added thereto. The resultant mixture went into suspension, whitened. From the mixture, the distillates having boiling points of between 65 to 70° C. were distilled off at atmospheric pressure, then, the mixture was subjected to further distillation under reduced pressure (5mmHg) to collect the distillates having boiling points of between 92 to 95 0C to provide 4-methyl-1,3-dioxolan-2-one. The yield of 4-methyl-1,3-dioxolan-2-one was 18.66 g (91 mole %) (1,2-propanediol basis), and its purity was not less than 99% (by gas chromatography).

After the distillation, there was left behind as a residue 2.06 g of white powder, and no polymerized compound was observed. The analysis of the water-soluble components of the residue by gas chromatography revealed the presence of 2 mole % of 1,2-propanediol therein (based on the 1,2-propanediol used). Adding up two figures: 2 mole % of 1,2-propanediol and the above-mentioned 91 mole % yield of 4-methyl-1,3-dioxolan-2-one, the material balance of the 1,2-propanediol used was 93 mole %.

Example 3 (Removal of an inactivated compound by filtration)

A mixture of 7.6 g (0.10 mol) of 1,2-propanediol (racemic body), 21.6 g (0.24 mol, 2.4 equiv.) of dimethyl carbonate, and 0.69 g (C.0050 mol, 0.05 equiv.) of $K_2CO_3$ was stirred at 30° C. for 3 hours. In the reaction mixture, there was formed the object compound 4-methyl-1,3-dioxolan-2-one with a 89% conversion of 1,2-propanediol and a 100% selectivity. The reaction mixture was cooled with an ice bath, and 0.50 g (1 equiv. relative to $K_2CO_3$) of concentrated sulfuric acid (purity: 98 weight %) was added thereto. Themixturewent into suspension, whitened. By filtering the reaction mixture through filter paper (5A size), solids (inactivated compound) were filtered off almost quantitatively.

Example 4 (Removal of an inactivated compound by two-layer separation)

A mixture of 15.2 g (0.20 mol) of 1,2-propanediol (racemic body), 27.0 g (0.30 mol, 1.5 equiv.) of dimethyl carbonate, and 1.38 g (0.010 mol, 0.05 equiv.) of $K_2CO_3$ was heated and refluxed for 3 hours. In the reaction mixture, there was formed the object compound 4-methyl-1,3-dioxolan-2-one with a 80% conversion of 1,2-propanediol and an approximately 100% selectivity. The reaction mixture was heated at atmospheric pressure to evaporate off the distillates having boiling points of between 65 to 75° C. The resultant mixture after the distillation was a colorless liquid with some polymerized compounds formed therein. To the residue was added 15.38 g of water, and the mixture was washed by stirring. Then, the mixture was allowed to stand over night and separated into the upper layer and the lower layer. The lower layer (organic layer) separated from the upper layer (water layer) was distilled under reduced pressure (1 mmHg), and 4-methyl-1,3-dioxolan-2-one was obtained by collecting the resultant distillates having boiling points of 87 to 90° C. The yield of 4-methyl-1,3-dioxolan-2-one was 13.01 g (64 mole t) (1,2-propanediol basis), and its purity was not less than 99% (by gas chromatography).

Example 5 (Distillation of 4-methyl-1,3-dioxan-2-one)

The operation was conducted in the same manner as in Example 2 except for using 18.0 g (0.20 mol) of 1,3-butanediol instead of 15.2 g of 1,2-propanediol. The object compound 4-methyl-1,3-dioxan-2-one was obtained with a 19.0 g yield (82 mole %) (1,3-butanediol basis). The structure of the product was characterized by comparing its $^1$H-NMR with that of the authentic sample.

Example 6 (Production of optically active 4-methyl-1,3-dioxolan-2-one)

Under a flow of nitrogen, a 100 ml four-neck flask equipped with a reflux condenser was fed with 9.45 g (0.124 mol; optical purity: 99.2%e.e.) of R-1,2-propanediol, 0.86 g (0.00622 mol, 0.05 equiv.) of potassium carbonate and 26.87 g (0.298 mol, 2.4 equiv.) of dimethyl carbonate. The mixture was stirred at 60° C. for 1 hour, and there was formed the object compound R-4-methyl-1,3-dioxolan-2-one with a 90% conversion of 1,2 -propanediol. The conversion approximately agreed with the conversion calculated from the equilibrium constant. Then, the heating and stirring were continued for another 30 minutes and consequently the reaction mixture went into suspension, having a pale-red color.

The reaction mixture was cooled with an ice bath, and 0.62 g (1 equiv. relative to $K_2CO_3$) of concentrated sulfuric acid (98 weight % purity) was added thereto to precipitate white solids out. The white solids were suction-filtered off through filter paper (5A size). The distillates having boiling points of 70° C. or lower were evaporated off from the filtrate at atmospheric pressure, then, the resultant residue was subjected to further distillation under reduced pressure (5 mmHg) using a Vigreaux column (200 mm) to collect the distillates having boiling points of between 91 to 92° C., and there was obtained R-4-methyl-1,3-dioxolan-2-one. The yield of R-4-methyl-1,3-dioxolan-2-one was 8.35 g , its purity was 98.5% (by gas chromatography), and its optical purity was 99.2%e.e. (by high performance liquid chromatography).

Comparative Example 1 (Catalyst: Ti(i-OPr)$_4$)

The operation was conducted in the same manner as in Example 1 except for using 1.43 g (0.050 mol, 0.05eq) of titanium tetraisopropoxide instead of 0.69 g of potassium carbonate anhydride. The object compound 5-methyl-1,3-dioxolan-2-one was obtained in a 5 mole % yield, with a 20% conversion of 1,2-propanediol and a 24% selectivity.

Comparative Example 2 (Catalyst: H-type strongly acidic cation-exchange resin)

The operation was conducted in the same manner as in Example 1 except for using 6.5 mL of Diaion RCPi60M instead of 0.69 g of potassium carbonate anhydride. On heating and refluxing for a period of 4 hours, the object compound 4-methyl-1,3-dioxolan-2-one was formed inanllmoletyield, with a 15% conversion of 1,2-propanediol and a 70% selectivity.

Comparative example 3 (Production by crystallization)

A mixture of 6.2 g (0.1 mol) of ethylene glycol, 21.6 g (0.24 mol, 2.4 equiv.) of dimethyl carbonate, and 0.69 g (0.0050 mol, 0.05 equiv.) of $K_2CO_3$ was heated and refluxed for 3 hours. The reaction mixture was added to 30 ml of ethanol, and the resultant mixture was cooled to 0° C. Then, the precipitate was filtered off. Upon recrystallization from ethanol,4.6 g of ethylene carbonate was precipitated in a 52 mole % yield (ethylene glycol basis).

What is claimed is:

1. A process for producing a cyclic ester, which comprises, in the presence of a salt of a weak acid with an alkali metal or alkaline earth metal, reacting a diol shown by the following formula (1):

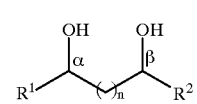

(1)

wherein n denotes an integer of 0 to 5, $R^1$ and $R^2$ are the same or different and each represents a hydrogen atom or unsubstituted straight- or branched-chain $C_{1-6}$ alkyl groups, and may bond together to form a ring together with the adjacent carbon atoms, with the proviso that $R^1$ and $R^2$ are not concurrently hydrogen atoms in the case of n=0 with a carbonic ester shown by the following formula(2):

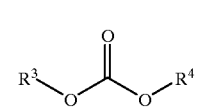

(2)

wherein $R^3$ and $R^4$ are the same or different and each represents a non-reactive organic group, and may bond together to form a ring together with the adjacent oxygen atoms to produce a cyclic carbonic ester shown by the following formula (3):

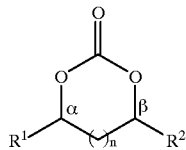

(3)

wherein $R^1$, $R^2$ and n have the same meanings as defined above.

2. A process for producing a cyclic carbonic ester according to claim 1, wherein said $R^1$ and $R^2$ are unsubstituted straight- or branched-chain $C_{1-6}$ alkyl groups, and said non-reactive organic groups represented by $R^3$ and $R^4$ are alkyl groups or aryl groups.

3. A process for producing a cyclic carbonic ester according to claim 1, wherein said diol shown by the formula (1) is a saturated $C_{3-10}$ alkylene glycol.

4. A process for producing a cylcic carbonic ester according to claim 1, wherein said carbonic ester shown by the formula (2) is a di-$C_{1-6}$ alkyl carbonate.

5. A process for producing a cyclic carbonic ester according to claim 1, wherein at least one of the carbon atoms at the α-position and the β-position of said diol shown by the formula (1) is asymmetric, and the cyclic carbonic ester is produced while retaining the steric configuration of the asymmetric carbon atom.

6. A process for producing a cyclic carbonic ester according to claim 1, wherein said weak acid is an acid having a pKa of 1 to 15.

7. A process for producing a cyclic carbonic ester according to claim 1, wherein said salt of weak acid is at least one member selected from the group consisting of carbonates, hydrogencarbonates, carboxylates and oxycarboxylates.

8. A process for producing a cyclic carbonic ester according to claim 1, wherein the amount of said carbonic ester (2) is 1 to 5 mole and the amount of said weak acid salt is 0.001 to 1 mole, relative to 1 mole of said diol (1).

9. A process for producing a cyclic carbonic ester according to claim 1, wherein a reaction mixture produced by the reaction of said diol shown by the formula (1) with said carbonic ester shown by the formula (2) is neutralized.

10. A process for producing a cyclic carbonic ester according to claim 9, wherein the neutralization is effected using 0.8 to 1.2 equivalent of an acid relative to a salt of a weak acid.

11. A process for producing a cyclic carbonic ester according to claim 9, wherein said reaction mixture is subjected to distillation after the neutralization.

12. A process for producing a cyclic carbonic ester according to claim 11, wherein the distillation is conducted at a temperature of 70 to 120° C.

13. A process for producing a cyclic carbonic ester according to claim 1, which comprises reacting a saturated $C_{3-6}$ alkylene glycol (1) having an asymmetric carbon atom or atoms with a di-$C_{1-2}$ alkyl carbonate (2) in the presence of a salt of a weak acid, neutralizing the resultant reaction mixture with an acid, and distilling the neutralized mixture at a temperature of 20 to 100° C. to produce an optically active cyclic carbonic ester, wherein the amount of the alkyl carbonate (2) is 2 to 10 mole relative to 1 mole of the alkylene glycol (1), and the amount of the salt of the weak acid is 0.01 to 0.2 mole relative to 1 mole of the alkylene glycol (1), and the amount of the acid is 0.9 to 1.1 equivalent relative to the salt of the weak acid.

* * * * *